United States Patent
Yang

(10) Patent No.: US 10,231,873 B2
(45) Date of Patent: Mar. 19, 2019

(54) AUTO DARKENING MASK

(71) Applicant: Ningbo Geostar Photoelectric Technology Co., Ltd, Zhejiang Province (CN)

(72) Inventor: Zhaolin Yang, Zhejiang Province (CN)

(73) Assignee: Global IP Services, PLLC

(*) Notice: Subject to any disclaimer, the term of this patent is extended or adjusted under 35 U.S.C. 154(b) by 409 days.

(21) Appl. No.: 15/136,996

(22) Filed: Apr. 25, 2016

(65) Prior Publication Data

US 2017/0042738 A1 Feb. 16, 2017

(30) Foreign Application Priority Data

Aug. 14, 2015 (CN) .................... 2015 2 0616193 U

(51) Int. Cl.
| | | |
|---|---|---|
| *A61F 9/06* | (2006.01) | |
| *G02F 1/133* | (2006.01) | |
| *A61F 9/00* | (2006.01) | |

(52) U.S. Cl.
CPC .......... *A61F 9/067* (2013.01); *G02F 1/13318* (2013.01)

(58) Field of Classification Search
CPC .......... A61F 9/023; A61F 9/045; A61F 9/067; A61F 9/06; A61F 9/061; G02F 1/13318
See application file for complete search history.

(56) References Cited

U.S. PATENT DOCUMENTS

| | | | | |
|---|---|---|---|---|
| 4,039,803 A | * | 8/1977 | Harsch ............... | A61F 9/062 2/8.4 |
| 4,241,286 A | * | 12/1980 | Gordon ............... | A61F 9/067 2/8.8 |
| 4,525,876 A | * | 7/1985 | Bailey ............... | A61F 9/061 2/8.3 |
| 4,620,322 A | * | 11/1986 | Eggenschwiler ....... | A61F 9/067 2/8.8 |
| 4,728,173 A | * | 3/1988 | Toth ............... | G02F 1/13475 219/147 |
| 4,863,244 A | * | 9/1989 | Fuerthbauer ......... | A61F 9/067 349/14 |
| 4,945,572 A | * | 8/1990 | Rosen ............... | A61F 9/061 2/8.3 |
| 5,074,647 A | * | 12/1991 | Fergason ............. | A61F 9/067 349/14 |
| 5,208,688 A | * | 5/1993 | Fergason ............. | A61F 9/067 349/104 |
| 5,224,219 A | * | 7/1993 | Edwards ............. | A61F 9/061 2/8.3 |
| 5,510,609 A | * | 4/1996 | Ackermann .......... | A42B 3/22 250/201.1 |
| 5,519,522 A | * | 5/1996 | Fergason ............. | A61F 9/067 219/147 |

(Continued)

*Primary Examiner* — Robert H Muromoto, Jr.
(74) *Attorney, Agent, or Firm* — Prakash Nama; Global IP Services, PLLC

(57) ABSTRACT

An auto darkening mask which has a weld cap and a filter mechanism, wherein the filter mechanism includes a lens module, a connecting line and a regulating system; and the weld cap is provided with a visible window. The lens module is assembled inside the weld cap and is opposite to the visible window of the weld cap. The regulating system protrudes out of an outer side of the weld cap and is connected with the weld cap, and the lens module is connected with and controlled by the regulating system through the connecting line.

9 Claims, 8 Drawing Sheets

(56) References Cited

U.S. PATENT DOCUMENTS

| | | | | |
|---|---|---|---|---|
| 6,012,163 | A * | 1/2000 | Holloway | A61F 9/061 2/8.3 |
| 6,021,520 | A * | 2/2000 | Wang-Lee | A61F 9/067 2/8.8 |
| 6,154,881 | A * | 12/2000 | Lee | A61F 9/045 2/9 |
| 6,185,739 | B1 * | 2/2001 | Verkic | A61F 9/06 2/8.1 |
| 6,230,328 | B1 * | 5/2001 | Holloway | A61F 9/061 2/8.3 |
| 6,710,298 | B2 * | 3/2004 | Eriksson | A61F 9/06 219/130.01 |
| 7,161,135 | B2 * | 1/2007 | Fergason | A61F 9/067 2/15 |
| 7,800,034 | B2 * | 9/2010 | Gerfin | A61F 9/023 250/201.1 |
| 8,081,262 | B1 * | 12/2011 | Perez | A61F 9/023 2/8.1 |
| 8,104,094 | B2 * | 1/2012 | Uttrachi | F16P 1/06 2/7 |
| 8,336,113 | B2 * | 12/2012 | Uttrachi | A61F 9/067 2/171.3 |
| 8,416,355 | B2 * | 4/2013 | Tamir | E06B 9/24 250/205 |
| 8,438,663 | B2 * | 5/2013 | Wright | A61F 9/064 2/8.2 |
| 8,502,866 | B2 * | 8/2013 | Becker | A61F 9/06 345/8 |
| 8,726,412 | B2 * | 5/2014 | Wright | A61F 9/064 2/10 |
| 8,776,263 | B1 * | 7/2014 | Fitos | A61F 9/062 2/8.3 |
| 8,953,104 | B2 * | 2/2015 | Ge | A61F 9/067 349/14 |
| 8,990,963 | B2 * | 3/2015 | Matthews | A61F 9/061 2/8.2 |
| 9,271,871 | B2 * | 3/2016 | Wright | A61F 9/064 |
| D753,345 | S * | 4/2016 | Yang | D29/110 |
| D756,569 | S * | 5/2016 | Yang | D29/110 |
| D785,563 | S * | 5/2017 | Yang | D13/103 |
| D786,787 | S * | 5/2017 | Yang | D13/103 |
| D788,032 | S * | 5/2017 | Yang | D13/107 |
| 9,655,784 | B2 * | 5/2017 | North | A61F 9/06 |
| D788,989 | S * | 6/2017 | Zhou | D29/110 |
| D793,008 | S * | 7/2017 | Yang | D29/110 |
| D793,009 | S * | 7/2017 | Yang | D29/110 |
| D793,626 | S * | 8/2017 | Yang | D29/110 |
| D793,955 | S * | 8/2017 | Yang | D13/107 |
| D796,118 | S * | 8/2017 | Yang | D29/110 |
| D805,256 | S * | 12/2017 | Yang | D29/110 |
| D806,318 | S * | 12/2017 | Yang | D29/107 |
| D809,129 | S * | 1/2018 | Yang | D24/110 |
| D809,130 | S * | 1/2018 | Yang | D24/110 |
| D810,274 | S * | 2/2018 | Yang | D24/110 |
| 9,889,045 | B2 * | 2/2018 | Matthews | A61F 9/061 |
| 9,918,018 | B2 * | 3/2018 | Beeson | A61F 9/06 |
| D814,406 | S * | 4/2018 | Yang | D13/107 |
| D814,407 | S * | 4/2018 | Yang | D13/107 |
| D814,408 | S * | 4/2018 | Yang | D13/107 |
| D814,409 | S * | 4/2018 | Yang | D13/107 |
| D820,205 | S * | 6/2018 | Yang | D13/107 |
| D821,314 | S * | 6/2018 | Yang | D13/110 |
| D821,971 | S * | 7/2018 | Yang | D13/107 |
| D823,789 | S * | 7/2018 | Yang | D13/107 |
| D825,457 | S * | 8/2018 | Yang | D13/107 |
| 10,052,233 | B2 * | 8/2018 | Yang | A61F 9/023 |
| 2005/0001155 | A1 * | 1/2005 | Fergason | A61F 9/067 250/221 |
| 2005/0007504 | A1 * | 1/2005 | Fergason | G01S 3/783 349/14 |
| 2007/0289049 | A1 * | 12/2007 | Gerfin | A61F 9/023 2/455 |
| 2008/0060102 | A1 * | 3/2008 | Matthews | A61F 9/061 2/8.2 |
| 2010/0299795 | A1 * | 12/2010 | Uttrachi | A61F 9/068 2/8.6 |
| 2011/0176072 | A1 * | 7/2011 | Ge | A61F 9/067 349/13 |
| 2011/0179541 | A1 * | 7/2011 | Wright | A61F 9/064 2/12 |
| 2011/0219506 | A1 * | 9/2011 | Uttrachi | A61F 9/067 2/8.6 |
| 2013/0160175 | A1 * | 6/2013 | Matthews | A61F 9/061 2/8.7 |
| 2013/0312151 | A1 * | 11/2013 | North | A61F 9/06 2/8.2 |
| 2014/0007312 | A1 * | 1/2014 | Wright | A61F 9/064 2/8.2 |
| 2015/0164694 | A1 * | 6/2015 | Matthews | A61F 9/061 2/8.2 |
| 2016/0022496 | A1 * | 1/2016 | DeKeuster | A61F 9/067 349/14 |
| 2016/0260261 | A1 * | 9/2016 | Hsu | G06T 19/006 |
| 2017/0035615 | A1 * | 2/2017 | Yang | A61F 9/06 |
| 2017/0042738 | A1 * | 2/2017 | Yang | A61F 9/067 |
| 2017/0252214 | A1 * | 9/2017 | Yang | A61F 9/023 |
| 2017/0289424 | A1 * | 10/2017 | Beeson | A61F 9/06 |
| 2018/0205868 | A1 * | 7/2018 | Beeson | A61F 9/06 |

* cited by examiner

AUTO DARKENING MASK

BACKGROUND OF THE INVENTION

The present invention relates to the field of human protection equipment, and in particular to an auto darkening mask.

Conventional auto darkening masks all comprise weld caps and filters. The filter is generally composed of a lens and a regulating system, wherein the regulating system is installed on the lens to be used for regulating a shade number, return time, sensitivity and an application mode of the lens. Since the lens and the regulating system are located in the weld cap, when the regulating system is used, only when the weld cap is taken off every time can the regulation be performed, and thus the operation is very troublesome.

BRIEF SUMMARY OF THE INVENTION

The object of the present invention is to overcome the aforementioned shortcomings in the prior art, and provide an auto darkening mask so that the problem that the operation is troublesome due to the fact that the weld cap needs to be taken off each time a regulating system is used can be solved To achieve the aforementioned object, the technical solution provided by the present invention is as follows: an auto darkening mask comprising a weld cap and a filter mechanism, wherein the filter mechanism includes a lens module, a connecting line and a regulating system; and the weld cap is provided with a visible window. The lens module is assembled inside the weld cap and is opposite to the visible window of the weld cap. The regulating system is located at the outside of the weld cap and connected with the weld cap, and the lens module is connected with and controlled by the regulating system through the connecting line.

In the auto darkening mask, the regulating system is installed on the left side or right side of the weld cap.

In the auto darkening mask, the regulating system comprises a control mechanism, a base and a circuit board, wherein the control mechanism and the base are located on the outer side and inner side of the weld cap respectively. The control mechanism comprises a sliding knob, a clamping cover, an indicator board and a first knob, wherein the indicator board is installed on the front of the clamping cover, and the first knob is located between the indicator board and the clamping cover. The base is installed on the back of the clamping cover and the circuit board is located between the clamping cover and the base. The circuit board is connected with a change-over switch which is connected with and controlled by the sliding knob and a first regulating switch which is connected with and controlled by the first knob. The first regulating switch has two different shade number waveband intervals, and the change-over switch can convert one shade number waveband interval and is matched with the first regulating switch to perform regulation.

In the auto darkening mask, the circuit board is further provided with a function module in a GRIND state, and the sliding knob may control the change-over switch to select and use the function module.

In the auto darkening mask, the top surface of the first knob has shade number waveband values corresponding to the two waveband intervals. The positions of the two shade number waveband values are distributed annularly around the axis of the first knob, and the diameters of distribution lines of the two shade number waveband values are different.

In the auto darkening mask, the indicator board is provided with a notch for displaying the two shade number waveband values.

In the auto darkening mask, the weld cap is provided with a mounting hole and the back of the clamping cover is provided with a step embedded in the mounting hole. The indicator board, the clamping cover and the base are fixedly combined through a screw, and thus the indicator board, the clamping cover, the base and the weld cap are fixedly connected.

In the auto darkening mask, the regulating system further comprises a battery electrically connected with the circuit board.

In the auto darkening mask, the back of the base is provided with a battery cavity for placing the battery and a battery cover for sealing the battery cavity.

In the auto darkening mask, the circuit board is further connected with two second regulating switches. The second regulating switches are equipped with second knobs enabling the second regulating switches to rotate, wherein one second regulating switch is used for regulating and sensing sensitivity of arc signals, and the other second regulating switch is used for regulating the time for restoring a shading state of a liquid crystal light valve to a bright state from a dark state.

Compared with the prior art, the present invention has the beneficial effects that:

1. According to the auto darkening mask, the filter mechanism is separated into the lens module and the regulating system which are positioned on the inner side and outer side of the weld cap respectively, and the lens module and the regulating system are connected through the connecting line. Therefore, in use, the regulating system can be used directly without needing to take off the weld cap, and the auto darkening mask is very convenient to operate and saves labor.

2. The first regulating switch in the regulating system has the two different shade number waveband intervals, and the change-over switch can convert one shade number waveband interval and is matched with the first regulating switch to perform regulation. The regulating system has convenience in regulation, and the regulatory range is expanded.

Figure 1:
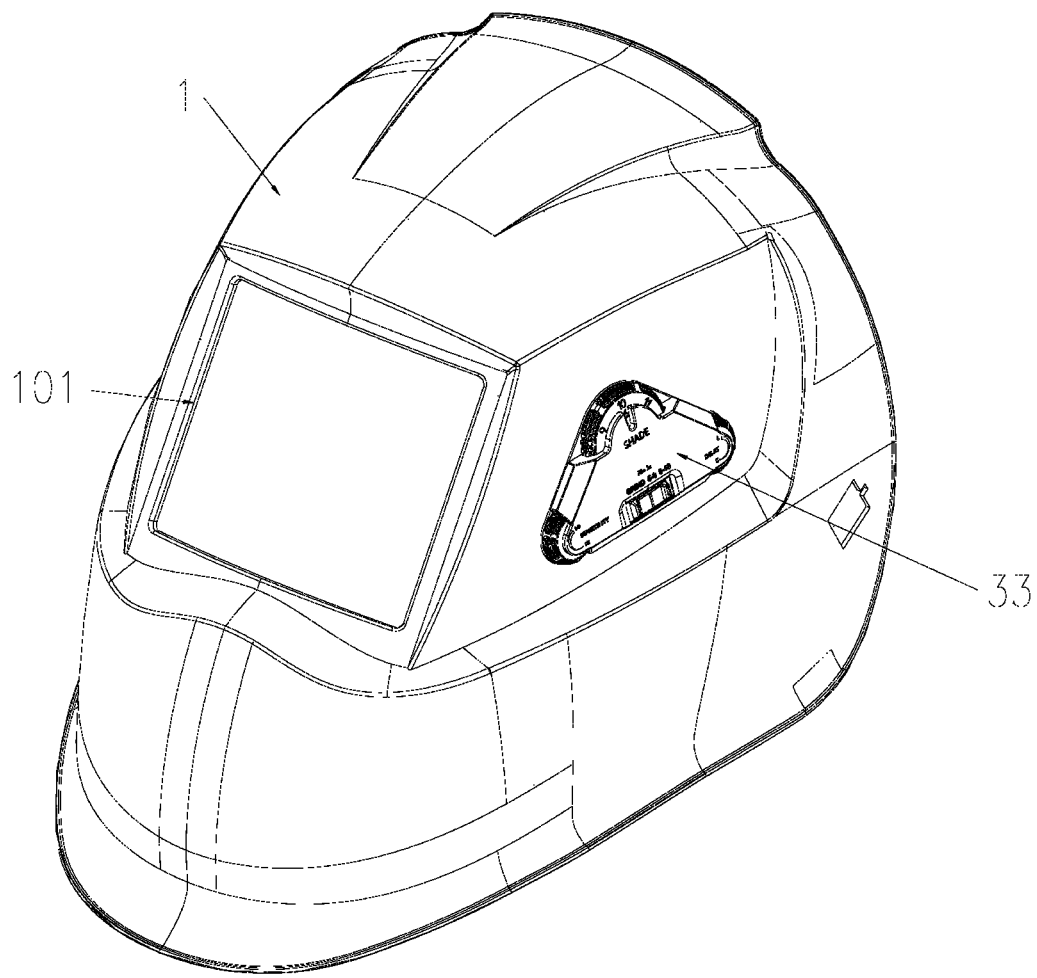
FIG. 1 is a first stereogram of an auto darkening mask according to the present invention.

In the drawings, there is a weld cap 1, a filter mechanism 3, a visible window 101, a lens module 31, a connecting line 32, a regulating system 33, a control mechanism 301, a clamping cover 302, a base 303, a sliding knob 305, an indicator board 306, a first knob 307, a circuit board 308, a change-over switch 309, a first regulating switch 310, shade number waveband values 111 and 222, second regulating switches 314, second knobs 315, a battery 311, a battery cavity 312, a battery cover 313 and a notch 316.

DETAILED DESCRIPTION OF THE INVENTION

The embodiments of the present invention are further described in detail in combination with drawings and embodiments below. The following embodiments are used for describing the present invention and are not used to limit the scope of the present invention.

Figure 2:
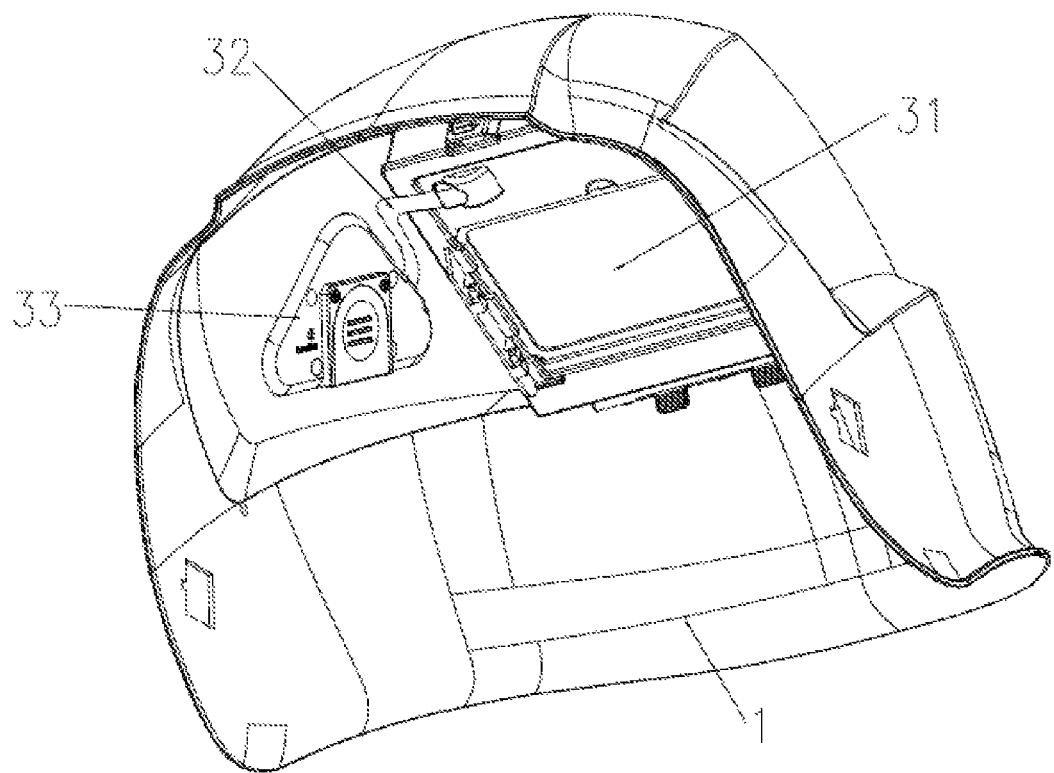
FIG. 2 is a second stereogram of an auto darkening mask according to the present invention.
Figure 3:
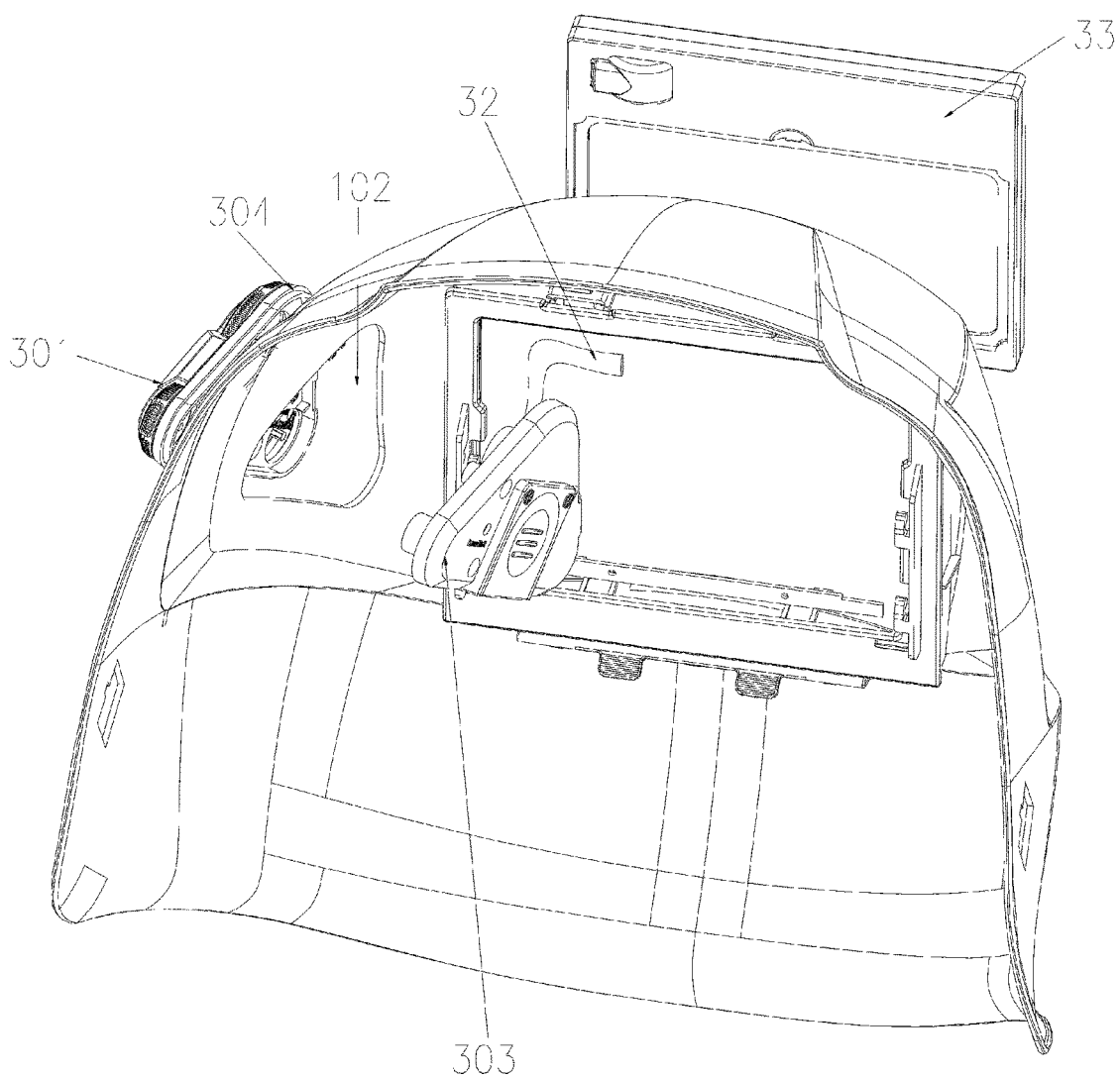
FIG. 3 is an exploded view of an auto darkening mask according to the present invention.
Figure 4:
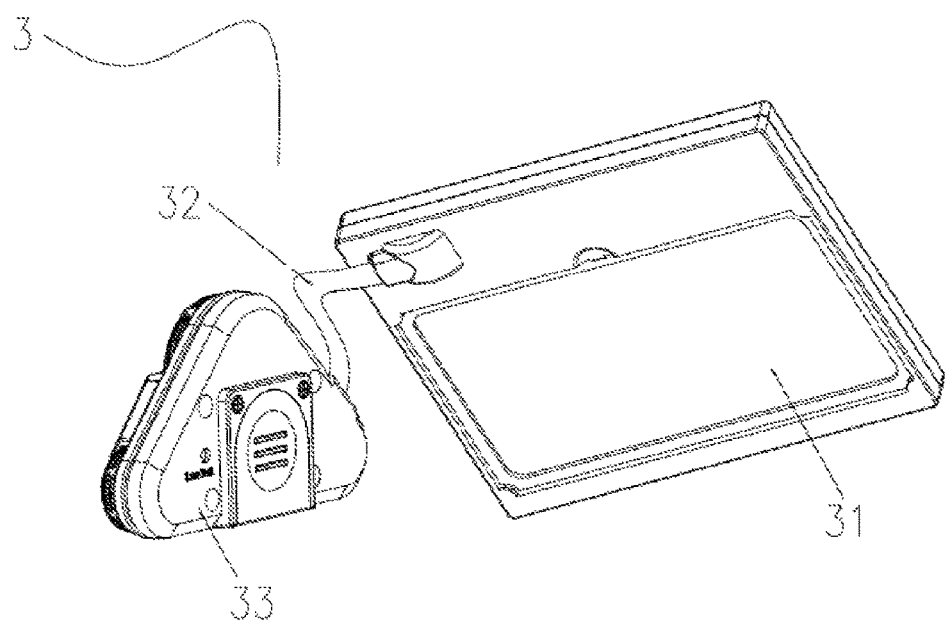
FIG. 4 is a stereogram of a filter mechanism according to the present invention.

As shown in FIGS. 1-4, the embodiment of the invention provides an auto darkening mask which comprises a weld cap 1 and a filter mechanism, wherein the filter mechanism includes a lens module 31, a connecting line 32 and a regulating system 33; and the weld cap 1 is provided with a visible window 101. The lens module 31 is assembled inside the weld cap 1 and is opposite to the visible window 101 of the weld cap 1. The regulating system 33 is located at the outside of the weld cap 1 and connected with the weld cap 1. In specific implementation, the regulating system 33 may be preferably installed on the left side or right side of the weld cap 1, and the lens module 31 is connected with and controlled by the regulating system 33 through the connecting line 32. Therefore, during the regulation, workers can use the regulating system directly without needing to taking off the weld cap, and thus the auto darkening mask is very convenient to operate and saves labor.

Figure 5:
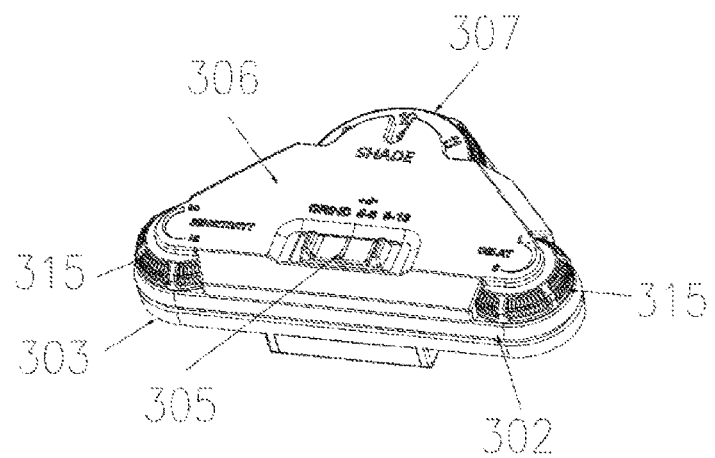
FIG. 5 is a stereogram of a regulating system according to the present invention.
Figure 6:
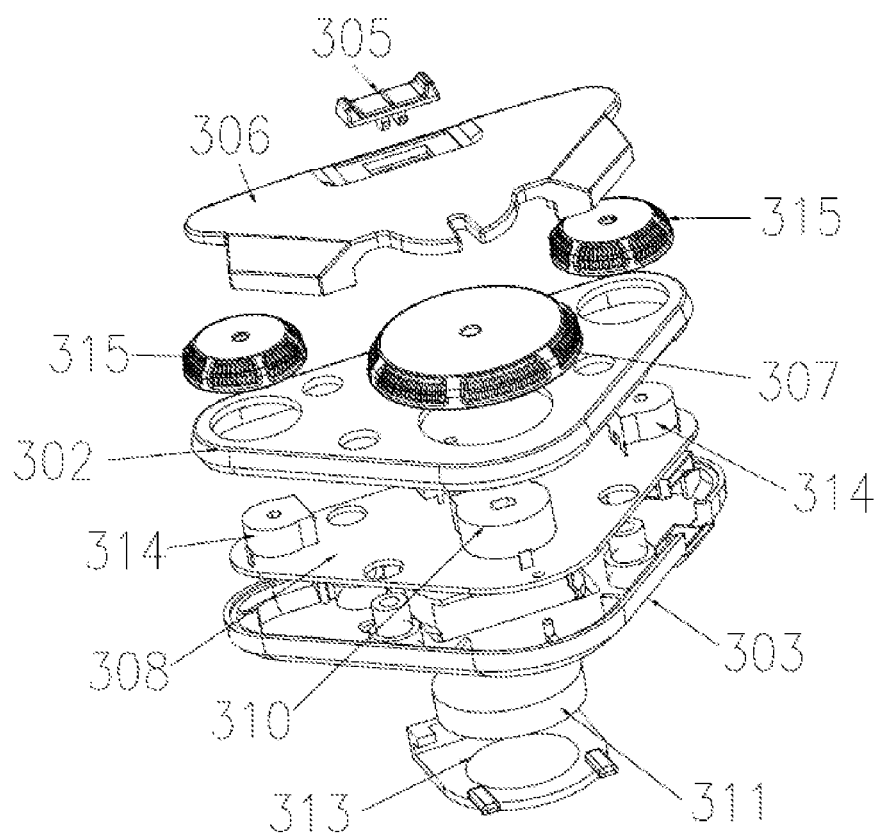
FIG. 6 is a first exploded view of a regulating system according to the present invention.
Figure 7:
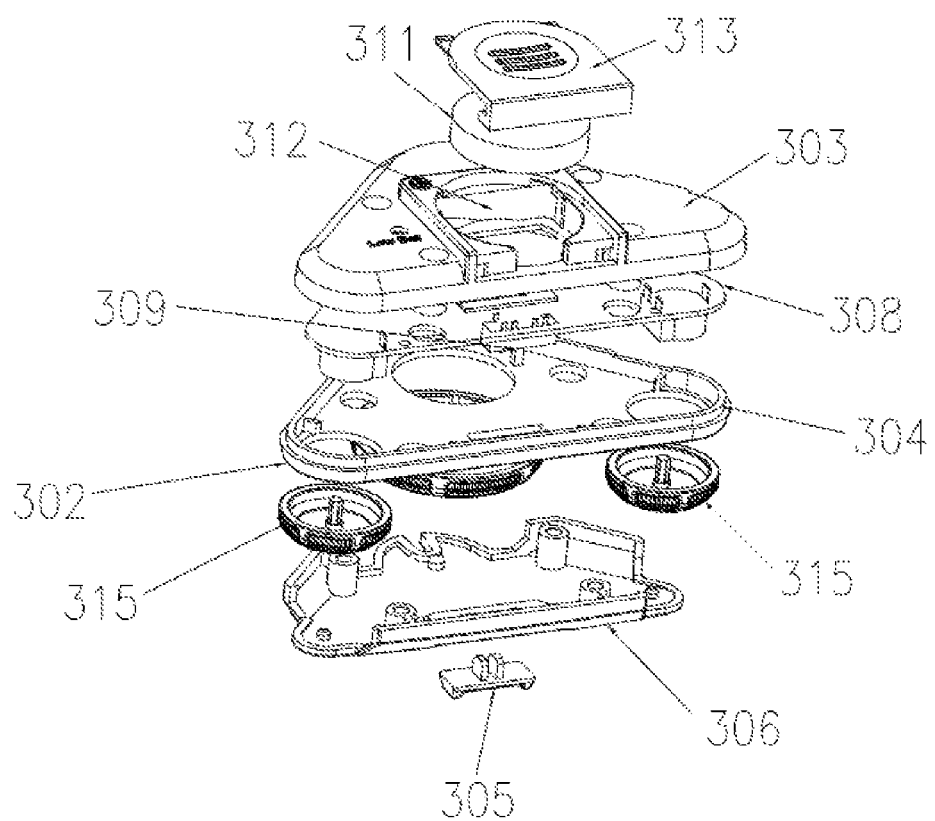
FIG. 7 is a second exploded view of a regulating system according to the present invention.
Figure 8:
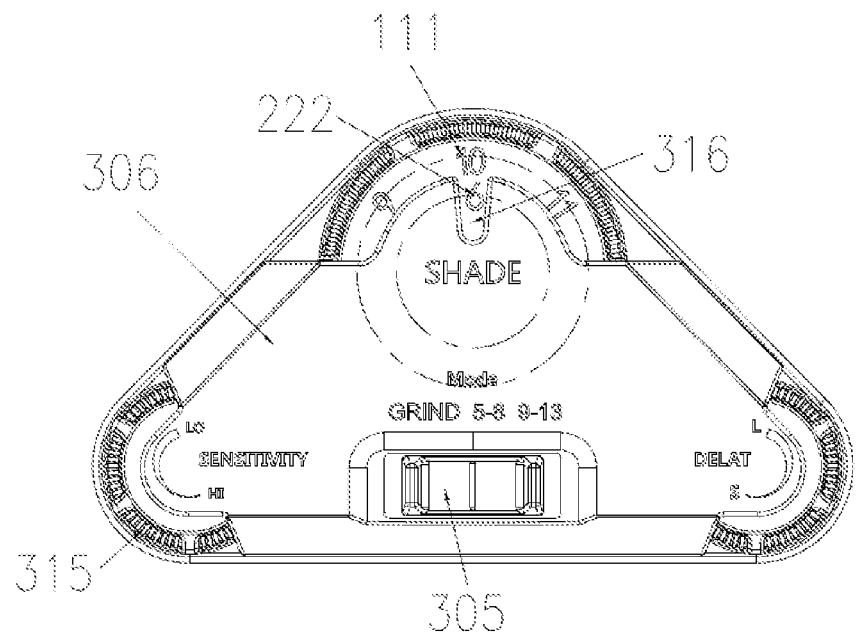
FIG. 8 is a plane view of a regulating system according to the present invention.
Figure 9:
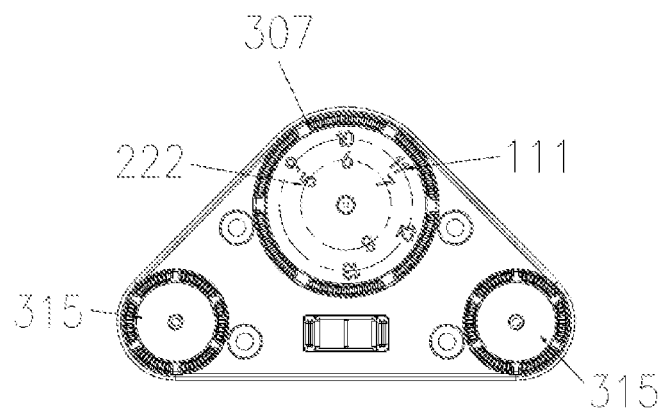
FIG. 9 is a plane view of a regulating system without an indicator board according to the present invention.
Figure 10:
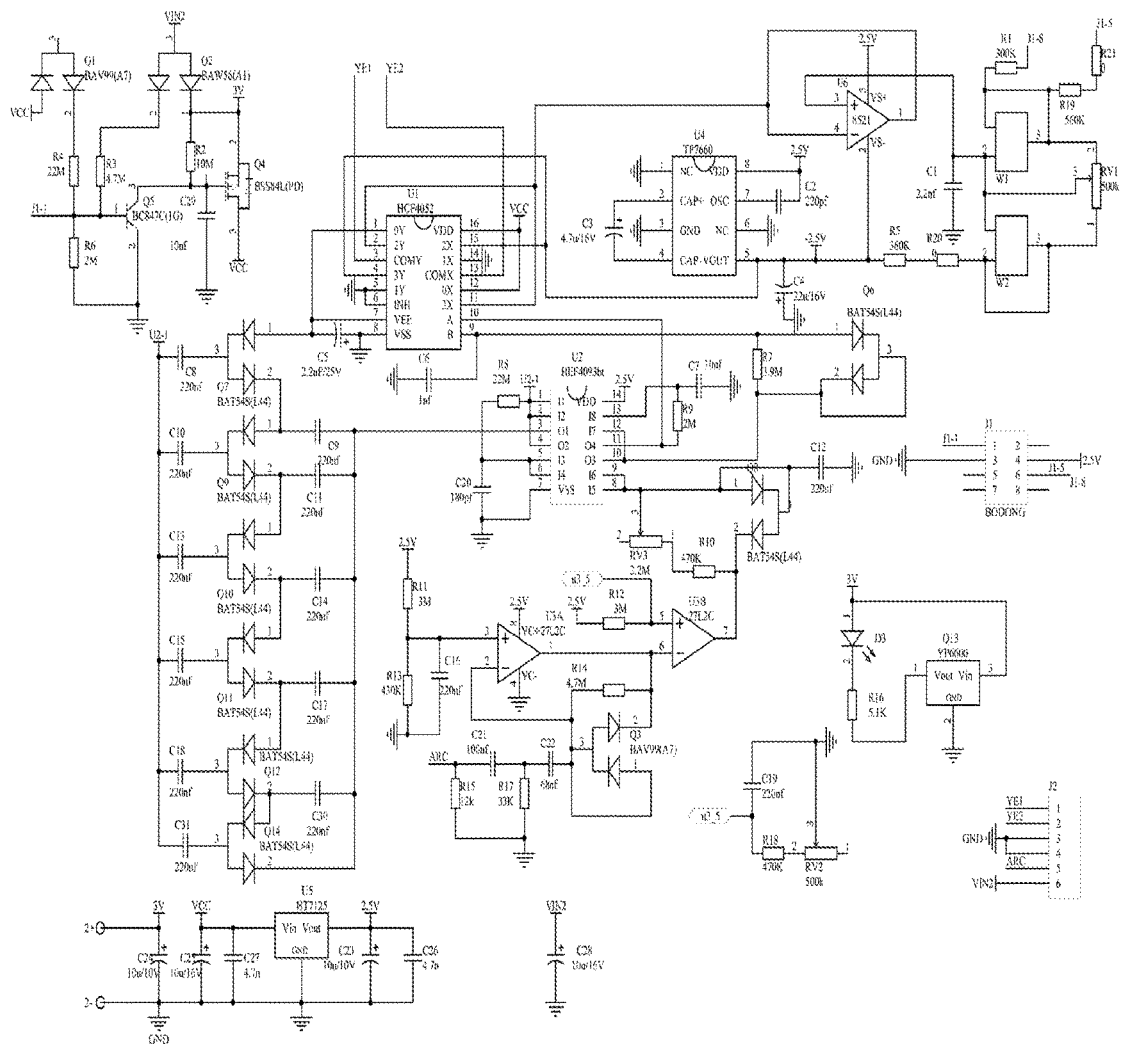
FIG. 10 is a circuit diagram of a regulating system according to the present invention.

As shown in FIGS. 5-10, the regulating system 33 comprises a control mechanism 301, a base 303 and a circuit board 308, wherein the control mechanism 301 and the base 303 are located on the outer side and inner side of the weld cap 1 respectively. The control mechanism 301 comprises a sliding knob 305, a clamping cover 302, second knobs 315, an indicator board 306 and a first knob 307, wherein the indicator board 306 is installed on the front of the clamping cover 302. The first knob 307 and the second knobs 315 are located between the indicator board 306 and the clamping cover 302. The base 303 is installed on the back of the clamping cover 302 and the circuit board 308 is located between the clamping cover 302 and the base 303. The circuit board 308 is connected with a change-over switch 309 which is connected with and controlled by the sliding knob 305, a first regulating switch 310 which is connected with and controlled by the first knob 307 and two second regulating switches 314 which are connected with and controlled by the respectively corresponding second knobs 315. The second knobs 315 are installed on the second regulating switches 314 and control the second regulating switches 314 to rotate. Moreover, the circuit board 308 is provided with a function module in a GRIND state, and the sliding knob 305 may control the change-over switch 309 to select and use the function module.

The first regulating switch 310 has two different shade number waveband intervals. The change-over switch 309 is of a three-section type toggle switch structure, wherein two section points are conversion points of the shade number waveband intervals, and the other section point is a conversion point which is used normally by the function module in a GRIND state. The top surface of the first knob 307 has shade number waveband values 111 and 222 corresponding to the two waveband intervals, wherein the range of the shade number waveband value 111 is 9-13, and the range of the shade number waveband value 222 is 5-8. The positions of the two shade number waveband values 111 and 222 are distributed annularly around the axis of the first knob 307, and the difference is that the diameters of distribution lines of the two shade number waveband values 111 and 222 are different. Therefore, when the auto darkening mask is in use, as long as the sliding knob 305 controls the change-over switch 309 to convert one shade number waveband interval to a usage state, the shade number waveband interval can be regulated through the first regulating switch 310, and thus the regulated range value is increased. The indicator board 306 is provided with a notch 316 for displaying the two shade number waveband values. During specific regulation, the first knob 307 is rotated with the notch 316 of the indicator board as a reference point so that the first regulating switch 310 can perform regulation according to the current bandwidth value. When a GRIND state is selected, the sliding knob 305 can control the change-over switch 309 to be converted to a corresponding section point, so that the function module can be used. According to the present invention, the regulation conversion of the two shade number waveband values and the GRIND state is implemented through the change-over switch 309, and thus the auto darkening mask is very simple in structure.

Concretely, the change-over switch 309 is applied to three working modes:

Mode 1: a GRIND state; at the time the shading degree of a liquid crystal light valve is in a minimum state, and this mode is generally used for polishing, etc.; the liquid crystal light valve does not need to be darkened, but the auto darkening mask still needs to be worn to achieve a certain protective effect.

Mode 2: a welded state with a shade number of 5-8; at the time the welding current is relatively small; however, for clearer observation, the shading degree of the liquid crystal light valve is in a small state. This mode is generally used for low current welding occasions of cutting, metal active gas (MAG) welding, tungsten inert gas (TIG) welding and micro-plasma welding and the like, and the liquid crystal light valve needs to be in a darkening state to a certain extent.

Mode 3: a shade number is 9-13, and this mode is generally used for large current welding such as TIG welding, MAG welding, MIG welding and plasma welding. The liquid crystal light valve needs to be in a dark state, so as to protect the human eyes from injury caused by strong light.

The number of the second regulating switches 314 is two, wherein one second regulating switch is used for regulating and sensing sensitivity of arc signals, and in a working state, the second regulating switch can enhance anti-interference to the environment and avoid false triggering. The other second regulating switch is used for regulating the time for restoring a shading state of the liquid crystal light valve to a bright state from a dark state. The return time can be set through the other second regulating switch, and the injury to human eyes caused by too bright welding spots during welding contact is avoided.

Concretely, the weld cap 1 is provided with a mounting hole 102 and the back of the clamping cover 302 is equipped with a step 304 embedded in the mounting hole 102. The indicator board 306, the clamping cover 302 and the base 303 are fixedly combined through a screw, and thus the indicator board 306, the clamping cover 302, the base 303 and the weld cap 1 are fixedly connected and accordingly clamped very firmly.

The regulating system 33 further comprises a battery 311 electrically connected with the circuit board 308. The back of the base 303 is equipped with a battery cavity 312 for placing the battery 311 and a battery cover 313 for sealing the battery cavity 312.

The aforementioned embodiments are preferred embodiments of the present invention, but the embodiments of the present invention are not subject to limitation of the aforementioned embodiments. Any other variation, modification, replacement, combination and simplification without departing from the spirit and principle of the present invention should be equivalent substitution modes and are included in the protection scope of the present invention.

What is claimed is:

1. An auto darkening mask, comprising a weld cap (1) and a filter mechanism, wherein the filter mechanism comprises a lens module (31), a connecting line (32) and a regulating system (33); the weld cap (1) is provided with a visible window (101); the lens module (31) is assembled inside the weld cap (1) and is opposite to the visible window (101) of the weld cap (1); the regulating system (33) protrudes out of an outer side of the weld cap (1) and is connected with the weld cap (1); and the lens module (31) is connected with and controlled by the regulating system (33) through the connecting line (32); the regulating system (33) comprises a control mechanism (301), a base (303) and a circuit board (308), wherein the control mechanism (301) and the base (303) are located on the outer side and inner side of the weld cap (1) respectively; the control mechanism (301) comprises a sliding knob (305), a clamping cover (302), an indicator board (306) and a first knob (307), wherein the indicator board (306) is installed on the front of the clamping cover (302); the first knob (307) is located between the indicator board (306) and the clamping cover (302); the base (303) is installed on the back of the clamping cover (302) and the circuit board (308) is located between the clamping cover (302) and the base (303); the circuit board (308) is connected with a change-over switch (309) which is connected with and controlled by the sliding knob (305) and a first regulating switch (310) which is connected with and controlled by the first knob (307); the first regulating switch (310) has two different shade number waveband intervals, and the change-over switch (309) may convert one shade number waveband interval and is matched with the first regulating switch (310) to perform regulation.

2. The auto darkening mask according to claim 1, wherein the regulating system (33) is installed on the left side or right side of the weld cap (1).

3. The auto darkening mask according to claim 1, wherein the circuit board (308) is further provided with a function mode used for polishing, and the sliding knob (305) may control the change-over switch (309) to select and use the function module.

4. The auto darkening mask according to claim 1, wherein the top surface of the first knob (307) has shade number waveband values (111 and 222) corresponding to the two waveband intervals; the positions of the two shade number waveband values (111 and 222) are distributed annularly around the axis of the first knob (307), and the diameters of distribution lines of the two shade number waveband values (111 and 222) are different.

5. The auto darkening mask according to claim 4, wherein the indicator board is provided with a notch (316) for displaying the two shade number waveband values (111 and 222).

6. The auto darkening mask according to claim 1, wherein the weld cap (1) is provided with a mounting hole (102) and the back of the clamping cover (302) is equipped with a step (304) embedded in the mounting hole (102); the indicator board (306), the clamping cover (302) and the base (303) are fixedly combined through a screw, and thus the indicator board (306), the clamping cover (302), the base (303) and the weld cap (1) are fixedly connected.

7. The auto darkening mask according to claim 1, wherein the regulating system (33) further comprises a battery (311) electrically connected with the circuit board (308).

8. The auto darkening mask according to claim 7, wherein the back of the base (303) is equipped with a battery cavity (312) for placing the battery (311) and a battery cover (313) for sealing the battery cavity (312).

9. The auto darkening mask according to claim 1, wherein the circuit board (308) is further connected with two second regulating switches (314), the second regulating switches (314) are equipped with second knobs (315) enabling the second regulating switches (314) to rotate, wherein one second regulating switch (314) is used for regulating and sensing sensitivity of arc signals, and the other second regulating switch (314) is used for regulating the time for restoring a shading state of a liquid crystal light valve to a bright state from a dark state.

* * * * *